US007163664B2

(12) United States Patent
Paskalov et al.

(10) Patent No.: US 7,163,664 B2
(45) Date of Patent: Jan. 16, 2007

(54) METHODS AND DEVICES FOR DISPENSING A POTABLE PRODUCT LIQUID

(75) Inventors: George Paskalov, Torrance, CA (US); Mark Gorodkin, Los Angeles, CA (US); Viktor Sokolov, Sherman Oaks, CA (US)

(73) Assignee: Hydro Enterprises, Inc., Van Nuys, CA (US)

( * ) Notice: Subject to any disclaimer, the term of this patent is extended or adjusted under 35 U.S.C. 154(b) by 359 days.

(21) Appl. No.: 10/663,216

(22) Filed: Sep. 15, 2003

(65) Prior Publication Data

US 2005/0056596 A1    Mar. 17, 2005

Related U.S. Application Data

(63) Continuation-in-part of application No. 10/432,208, filed as application No. PCT/US01/49310 on Dec. 20, 2001.

(60) Provisional application No. 60/258,208, filed on Dec. 27, 2000.

(51) Int. Cl.
    *B01J 19/08*    (2006.01)
(52) U.S. Cl. .................... 422/186.29; 422/186
(58) Field of Classification Search .......... 422/186.29, 422/186.04, 186
    See application file for complete search history.

(56) References Cited

U.S. PATENT DOCUMENTS

| 4,954,320 | A | | 9/1990 | Birmingham et al. .. 422/186.04 |
|---|---|---|---|---|
| 5,387,324 | A | | 2/1995 | Ibbott et al. ................. 204/150 |
| 5,624,544 | A | | 4/1997 | Deguchi et al. ............. 205/742 |
| 5,651,887 | A | * | 7/1997 | Posner et al. ................ 210/232 |
| 5,656,171 | A | | 8/1997 | Strachwitz ................... 210/695 |
| 5,824,353 | A | | 10/1998 | Tsunoda et al. ............... 426/66 |
| 5,866,010 | A | | 2/1999 | Bogatin et al. ............. 210/695 |
| 5,876,663 | A | * | 3/1999 | Laroussi ...................... 422/23 |
| 5,965,009 | A | | 10/1999 | Shimamune et al. ....... 205/742 |
| 5,997,590 | A | | 12/1999 | Johnson et al. ............... 44/301 |
| 6,033,678 | A | | 3/2000 | Lorenzen .................... 424/401 |
| 6,165,339 | A | | 12/2000 | Ibbott ......................... 204/554 |
| 6,453,799 | B1 | * | 9/2002 | Kown .......................... 99/286 |
| 6,609,687 | B1 | * | 8/2003 | Leski ....................... 248/188.2 |

FOREIGN PATENT DOCUMENTS

JP          11-253522       9/1999

\* cited by examiner

*Primary Examiner*—Kishor Mayekar
(74) *Attorney, Agent, or Firm*—Rutan & Tucker, LLP

(57) ABSTRACT

An apparatus subjects water to waves from an RF plasma. This allows continuous production of "activated water" characterized by cluster sizes below about 4 molecules per cluster, substantially bacteria free water and controlled pH. The basic frequency of the plasma is preferably between 0.44 MHz and 40.68 MHz, and the plasma is preferably modulated at a frequency between 10 kHz and 35 kHz. Flow rates typically range from 20 l/hr to about 2000 l/hr. Activated water can be used for many purposes, including antimicrobial treatment of drinking water, antimicrobial cleaning of worktables, floors, walls, knives, and other surfaces, for example, in meat processing facilities and hospitals.

15 Claims, 1 Drawing Sheet

METHODS AND DEVICES FOR DISPENSING A POTABLE PRODUCT LIQUID

This application is a Continuation-In-Part of patent application Ser. No. 10/432,208 filed Sep. 22, 2003 which claims priority to PCT patent application No. PCT/US01/49310 filed on Dec. 20, 2001 which claims priority to patent application No. 60/258,208 filed Dec. 27, 2000.

FIELD OF THE INVENTION

The field of the invention is liquid dispensers.

BACKGROUND

Water dispensing devices can be classified as free standing or coupled to an online source of water. For purposes of this application a device that is coupled to an online source has a connection to an external (i.e. separate from the dispensing device) source of water that is typically replenished by nature. These including a reservoir, a lake, a river, and an in ground wells A free standing water dispensing device has no connection to an external water source and therefore generally dispenses either a pre-bottled product or a product that is drawn from a receptacle stored inside the dispensing device itself. Free standing water dispensers are pervasive because of the ease with which water can be disinfected and bottled off-site. Such free standing dispensers, however, run dry and require relatively frequent replenishment.

Water dispensing devices that are coupled to online sources are advantageous in that the source of water is not limited by the size of a container or the number of containers that the device can hold. A disadvantage, however, of coupling to an online source is that disinfection of the water is typically done by the dispensing device. This adds to the cost and complexity of the dispensing device, but in many countries water disinfection is a necessity because of the high content of parasites, protozoa, bacteria, viruses, and so on.

Thus, in order to use an online water source, it is desirable for the water dispensing device itself to be capable of disinfecting the water. Among the more common methods used to disinfect water from an online source are ion exchange, reverse osmosis filters, chemicals, and even ultraviolet disinfecting. Systems that utilize reverse osmosis filters or chemicals generally require too much attention in that the filters need to be cleaned or replaced and the chemicals need to be maintained at appropriate levels.

Ion exchange and ultraviolet systems generally work well, however, it is desirable to be able to produce small cluster water defined herein to mean a size of only 5–6 water molecules per cluster, and these methods are not effective at producing such results. Small cluster water is reported to have numerous useful characteristics. Among other things, small cluster water is said to provide: improved taste of foods; accelerated absorption of drugs and food through the digestive tract; and prevention of cancer due to reduced production of mutagens in the intestines and reduced activity of enteric microorganisms and digestive tract tissue cells. See U.S. Pat. No. 5,824,353 to Tsunoda et al. (October 1998). Tsunoda et al. and all other publications identified herein are incorporated by reference in their entirety.

In producing small cluster water, electrical, magnetic, chemical, and acoustical methods have all been utilized. Electrical and magnetic methods typically involve running water past closely spaced electrodes. Examples are set forth in U.S. Pat. Nos. 5,387,324 (February 1995) and U.S. Pat. No. 6,165,339 (December 2000), both to Ibbott. Usually field strength is adjusted by moving the electrodes or magnets with respect to one another. See, e.g., U.S. Pat. No. 5,866,010 to Bogatin et al. (February 1999). In other instances field strength is adjusted by altering the path of the water. See e.g. U.S. Pat. No. 5,656,171 to Strachwitz (August 1997), which describes curved piping through magnetic field. U.S. Pat. No. 6,033,678 (March 2000) and U.S. Pat. No. 5,711,950 (January 1998) both to Lorenzen, describe production of reduced cluster water by passing steam across a magnetic field.

Chemical methods typically involve adding electrolytes and polar compounds. The U.S. Pat. No. 5,824,353 patent to Tsunoda, et al. teaches production of reduced cluster size water using a potassium ion concentration of 100 ppm or more, and containing potassium ions, magnesium ions and calcium ions in a weight ratio of potassium ions:magnesium ions : calcium ions of 1: 0.3–4.5:0.5–8.5. Other chemical methods include use of surfactants, and clathrating structures that cause inclusion of one kind of molecules in cavities or lattice of another. See U.S. Pat. No. 5,997,590 to Johnson et al. (issued December 1999).

Acoustical methods typically involve subjection of water to supersonic sound waves. See U.S. Pat. No. 5,997,590 to Johnson et al. (issued December 1999).

A Japanese company currently sells a water purifying system that is said to produce water having cluster size of 5–6 molecules. The system, marketed under the name Microwater™, passes tap water past electrodes. Water passing closer to a positive electrode tends to become acidic. The company's literature reports that the acidic water (termed oxidized or hyperoxidized water) is said to be useful as an oxidizing agent to sterilize cutting boards and treat minor wounds. Other suggested uses are treating athlete's foot, minor burns, insect bites, scratches, bedsores and postoperative wounds. The company's literature also reports that the acidic water has been used agriculturally to kill fungi and other plant diseases. Water passing closer to a negative electrode tends to become alkaline. The alkaline water (termed reduced water) is said to be beneficial when taken internally. Such water is said to inhibit excessive fermentation in the digestive tract by indirectly reducing metabolites such as hydrogen sulfide, ammonia, histamines, indoles, phenols, and scatols.

U.S. Pat. No. 5,624,544 to Deguchi et al. (April 1997) describes such a system. Deguchi et al. claim that oxidizing streams down to pH 4.5 and reducing streams up to pH 9.5 can be achieved on a continuous basis, but that waters having pH 2.5 to 3.2 or pH 11.5 to 12.5 cannot be produced continuously for a long period. It is thought that these limitations are due to the known methods and apparatus being incapable of efficiently reducing the cluster size below about 4 molecules per cluster.

Thus, there is still a need to provide methods and apparatus for dispensing potable liquids that can continuously produce substantial quantities of water having little or no bacteria, having cluster sizes below about 4 molecules per cluster, and all without substantially changing the pH. Water having these characteristics is thought to be much more safe and active than other known waters.

SUMMARY OF THE INVENTION

The present invention provides methods and apparatus for dispensing a potable product liquid derived from an online source. Within the water dispensing device, the source liquid travels through a conduit and is subjected to waves from an RF plasma generator in order to produce a treated liquid. The product of the dispensing device includes at least some of the treated liquid and frequently includes additives such as flavoring and carbonation.

Methods of dispensing a potable liquid can include the steps of providing a source of water contaminated with microorganisms, generating waves using an RF plasma generator, producing treated water by passing the contaminated water past the waves under conditions that kill at least 95% of the microorganisms, and dispensing the treated water. Further contemplated steps includes combining the treated water with flavoring and other chemicals.

Various objects, features, aspects, and advantages of the present invention will become more apparent from the following detailed description of preferred embodiments of the invention, along with the accompanying drawing.

DETAILED DESCRIPTION

Figure 1:
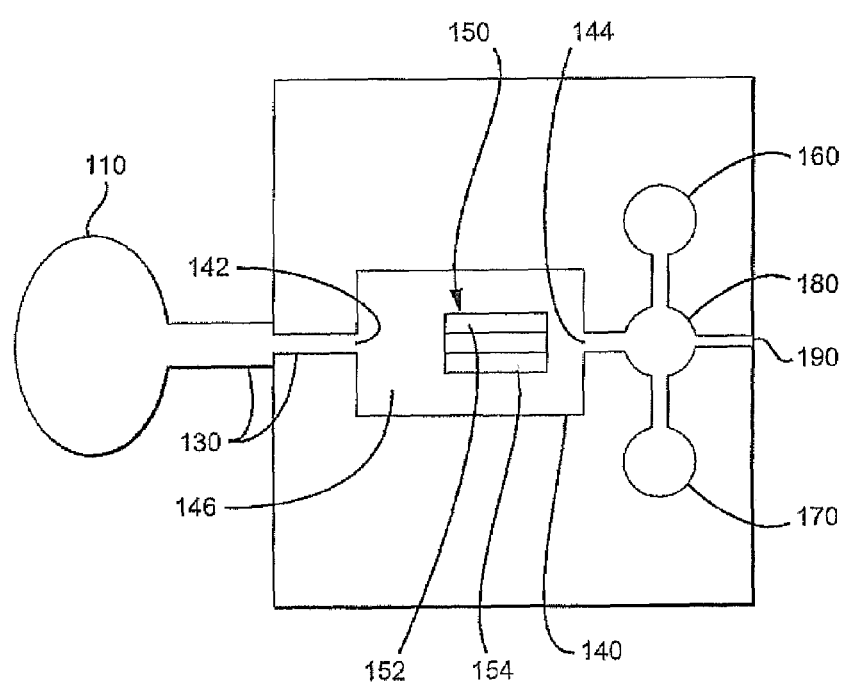
FIG. 1 is a cross sectional view of a water dispensing device.

Referring to FIG. 1, a dispenser for dispensing a potable product comprises an online source of a source liquid 110, an RF plasma wave generator 150, a conduit 130, a flavoring source 160, a carbonation source 170, a mixer 180, and a dispensing line 190.

A reaction chamber 140 houses the RF plasma wave generator 150 including electrodes 152, 154. It is within the reaction chamber that the source liquid is treated to the waves from the RF plasma wave generator. As such, it is advantageous for the reaction chamber to be substantially liquid impermeable and for the input and output valves (not shown) to only allow flow in or out, respectively. Reaction chamber 140 is preferably constructed of stainless steel to reduce corrosion effects, although any sufficiently strong and resistant material could be used, including for example titanium, tantalum, stainless steel coated with titanium, molybdenum, platinum,iridium, and so forth.

Reaction chamber 140 can be any suitable size and shape, as long the source liquid being treated is subjected to energy from the plasma under conditions that produce the desired characteristics in the treated water. Thus, although the reaction chamber 140 in FIG. 1 is preferred to have a circular cross-section, other suitable chambers may have a polygonal, oval or other horizontal cross section. Small units are contemplated, for example, where the reaction chamber is only about 200 ml or less. On the other hand large units are contemplated that have an internal volume of at least 10l, as well as everything in between. Unless otherwise stated, ranges are deemed herein to be inclusive of the stated endpoints.

A preferred class of apparatus subjects water to waves from an RF plasma wave generator 150. Specific aspects of subjecting water to an RF plasma wave generator are taught in pending U.S. patent application Ser. No. 10/432208 incorporated by reference in its entirety. The basic frequency of the plasma is preferably between 0.44 MHz and 40.68 MHz, and the plasma is preferably modulated at a frequency between 10 kHz and 34 kHz. Flow rates typically range from 20 l/hr to about 2000 l/hr, although multiple configurations and sizes of device are also contemplated, so that lower and higher flow rates are possible.

Plasmas are conductive assemblies of charged particles, neutrals and fields that exhibit collective effects. Plasma generator 150 is preferably a "cold" type plasma device, which term is used herein to mean a gas of ionized atoms cooler than 10,000° K. With the plasma generator 150 in operation, a stream of source liquid 100 enters the reaction chamber 140 at inlet 142, flows through inner space 146, and exits the reaction chamber 140 through outlet 144. It should be noted that multiple inputs and multiple online sources are also contemplated. Moreover, the reaction chamber may accept input from both an online source as well as a resident source. Thus, FIG. 1 could be amended such that flavor source 160 and carbonation source 170 are input to the reaction chamber 140 rather than the mixer 180.

Source liquid 110 is considered to be online to the dispensing device. This means that the source liquid is derived from a source outside of the dispensing device. For example, a well can be the online source for the source liquid. More preferably, however, a source liquid is pumped from a municipal water outlet (municipal source) such as reservoir or a water tower. In any case, the online source is typically coupled to the water dispensing device through a series of pipes (i.e. conduits). In the case of a local well, however, it is contemplated that there may be only a single pipe running from the online source to the dispensing device.

Source liquid is contaminated to some degree with parasites (e.g. *schistosoma*), protozoa (e.g. *cryptosporidium parvum*), bacteria (e.g. *cholera*), viruses (e.g. hepatitis A), and/or metals, perchlorates and other abiotic substances. In a preferred class of embodiments of the device and in preferred methods of dispensing, the waves kill at least 99.9% of the microorganisms. The treated liquid and potable product liquid are therefore preferred to be 99.9% free of microorganisms. It is contemplated that the source liquid can have substantially any practical purity. Tap water is thought to typically contain between about 95% $H_2O$ and is considered to be a good online source of the source liquid. Distilled water is less suitable because it contains little or no dissolved salts. When processed water has some electro-conductivity it is easier to match plasma and water parameters using the standard matching network system.

Conduit 130 is preferred to be a pipe or series of pipes generally extending from the online source to and into the reaction chamber. The conduit treats the source liquid to the waves in that it introduces the source liquid to the reaction chamber within which the source liquid is subjected to the waves. Along a path from the online source to the dispensing device, the size and composition of the conduit may change many times. For example, the conduit may be a cement channel at one point along the path, a pvc pipe at another point, a copper pipe at another, a flexible tube at another, and so on. Application of waves to a source liquid generally creates separate streams—one substantially basic and one substantially acidic. The two streams are combined to form the treated liquid.

Mixer 180 is an area where a treated liquid (i.e. already subjected to RF plasma waves) and additional chemicals are combined. In a preferred class of embodiments, a fountain drinks is the potable product liquid that is dispensed by the dispenser. FIG. 1 shows a flavor source 160 which is container having a flavored syrup such as coke flavor, cherry flavor, or root beer flavor. In addition to the flavor source, a carbonation source 170 can be added to the mixer. It should be noted that additional chemicals not mentioned here including vitamin supplements, alcohol, and fruit juices can be mixed with the treated liquid. The mixed product (the potable product liquid) is dispensed from the machine for the consumer.

A potable product liquid can consist only of a treated liquid, however, in most preferred embodiments, some additional chemicals are added. Consider the example of a soft drink dispenser. In this example, the source liquid is water, the carbonation source is a carbonator, and the flavor source may be Coke™ flavoring. The carbonator, the treated water, and the Coke™ flavoring will be combined and mixed in the mixer before being dispensed to the consumer.

Because the carbonator and the Coke™ flavoring have not been subjected to the waves, it is possible that the microorganism content of the product liquid will be raised by the addition of the carbonator and/or flavoring. A more preferred embodiment may, therefore, include subjecting the additional chemicals or components (e.g. the flavoring) to the RF plasma waves so that the entire potable product liquid has been subjected to the waves. In an embodiment in which the additional chemicals are also subjected to the waves, it may be advantageous to mix the additional chemicals and the source liquid before subjecting the mixture to the waves. Alternatively, the additional chemicals and the source liquid can be subjected to the waves in sequence. By subjecting the additional chemicals and the source liquid to the waves separately (i.e. in sequence) the RF plasma generator can be programmed to use different settings for each chemical.

Those skilled in the art will recognize that the device of FIG. 1 can be scaled up or down. For example, the device of FIG. 1 can alternatively be viewed as having multiple inputs and multiple outputs so long as at least some of the source liquid is subjected to the waves of the RF plasma wave generator. The dispenser itself may resemble a typical soft drink dispenser as is common in restaurants. It may, however, have another configuration including that of a water vending machine, and in such a configuration, the dispenser can have a money slot for inserting money and change slot for returning money. Additionally, it is contemplated that the dispenser, or at least the reaction chamber, is protected by some sort of lock or security system in order to protect the RF plasma.

Methods of dispensing a potable liquid include the steps of providing a source of contaminated water, generating wave using a RF plasma generator, producing treated water by passing the contaminated water pas the waves under conditions that kill at least 95% of the microorganisms, and dispensing the treated water.

The contaminated water can have from a relatively high degree of contamination to a relatively low degree of contamination, but in any case, exposure to the RF plasma destroys additional microorganisms making the water comparatively more safe and pure. The source of the contaminated water can be an online source or even a stand alone source such as a container of contaminated water. It is important to realize that the term water is intended to include liquids that contain varying content of water, although the preferred water sources do typically contain a high content of water.

In generating waves using an RF plasma generator, the RF plasma generator is operated within the ranges outlined above. The waves from the RF plasma come in contact with the contaminated water thereby producing treated water. It may be desirable to further treat the treated water by subjecting the treated water to filtering, reverse osmosis, and so on. Additionally, it may be advantageous to combine additional chemicals (i.e. flavors, supplements, and so on) with the treated water prior to dispensing.

Thus, specific embodiments and applications directed toward dispensing of a potable product liquid have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A dispenser for dispensing a potable product liquid comprising:
   an on-line source of a source liquid having a chemical composition; a first electrode and a second electrode;
   a RF plasma wave generator configured to produce a plasma in a space between first and second electrodes, the plasma producing waves, and
   a conduit configured to treat the source liquid to the waves external to the space to produce a treated liquid, and the product liquid includes at least some of the treated liquid, without altering the chemical composition of the liquid.

2. The liquid dispenser of claim wherein the on-line source comprises a municipal water outlet.

3. The liquid dispenser of claim 1 wherein the conduit passes the treated liquid to an outlet without adding any additional chemical.

4. The liquid dispenser of claim 1 further comprising a mixer that mixes the treated liquid with a flavoring.

5. The liquid dispenser of claim 1 further comprising a canister containing a soft drink syrup, and a mixer that mixes at least some of the treated liquid with at least some of the syrup.

6. The liquid dispenser of claim 1 further comprising a canister containing a carbonator, and a mixer that mixes at least some of the treated liquid with at least some of the carbonator.

7. The liquid dispenser of claim 1 further comprising a locked cabinet that includes the RF plasma wave generator.

8. The liquid dispenser of claim 1 further comprising a locked cabinet that includes a money slot.

9. The liquid dispenser of claim 1 further comprising a display that displays a price for the product liquid.

10. The liquid dispenser of claim 1 wherein the conduit carries the source liquid in at least two substantially separate streams past the waves, and then recombines the separate streams.

11. The liquid dispenser of claim 1 further comprising a charcoal filter fluidly positioned between the on-line source and a product liquid dispenser.

12. The liquid dispenser of claim 1 wherein the on-line source provides unhealthy amount of a microorganism.

13. The liquid dispenser liquid dispenser of claim 12 wherein the microorganism is selected from the group consisting of *E. coli Salmonella, Hepatitis A, Cryptosporidium Parvum,* and *Polio*.

14. The liquid dispenser of claim 1 wherein the RF plasma wave generator has a basic frequency of 0.44 Mhz–40.56 MHz.

15. The liquid dispenser liquid dispenser of claim 1 wherein the RF plasma wave generator has a modulation frequency of 10–35 kHz, a pulse amplitude of 2–40 kV, a pulse width of 5–45 microseconds, and a repetition rate of 10–35 kHz.

* * * * *